United States Patent
Eshelman et al.

(10) Patent No.: US 9,433,348 B2
(45) Date of Patent: Sep. 6, 2016

(54) METHOD OF RENDERING HEMODYNAMIC INSTABILITY INDEX INDICATOR INFORMATION

(71) Applicant: KONINKLIJKE PHILIPS N.V., Eindhoven (NL)

(72) Inventors: Larry James Eshelman, Ossining, NY (US); Abigail Acton Flower, Mahopac, NY (US); Brian David Gross, North Andover, MA (US); Joseph James Frassica, Gloucester, MA (US); Larry Nielsen, Burlington, MA (US); Mohammed Saeed, Cambridge, MA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 113 days.

(21) Appl. No.: 14/401,987

(22) PCT Filed: May 6, 2013

(86) PCT No.: PCT/IB2013/053612
§ 371 (c)(1),
(2) Date: Nov. 18, 2014

(87) PCT Pub. No.: WO2013/171620
PCT Pub. Date: Nov. 21, 2013

(65) Prior Publication Data
US 2015/0145691 A1    May 28, 2015

Related U.S. Application Data

(60) Provisional application No. 61/648,838, filed on May 18, 2012.

(51) Int. Cl.
*A61B 5/00* (2006.01)
*G06F 19/00* (2011.01)
*A61B 5/021* (2006.01)
*A61B 5/024* (2006.01)

(52) U.S. Cl.
CPC .......... *A61B 5/0002* (2013.01); *A61B 5/7275* (2013.01); *A61B 5/746* (2013.01); *A61B 5/7425* (2013.01); *G06F 19/345* (2013.01); *G06F 19/3418* (2013.01); *G06F 19/3431* (2013.01); *G06F 19/3443* (2013.01); *A61B 5/021* (2013.01); *A61B 5/024* (2013.01)

(58) Field of Classification Search
CPC .............. A61B 5/0002; A61B 5/7275; G06F 19/3431
See application file for complete search history.

(56) References Cited

U.S. PATENT DOCUMENTS 5,357,976 A * 10/1994 Feng .................. A61B 5/04004
600/544
2008/0214904 A1     9/2008 Saeed et al.

OTHER PUBLICATIONS

Cao, H. et al. "Preducting ICU hemodynamic instability using continuous multiparameter trends", Engineering in Medicine and Biology Society, 2008, 30th Annual International Conference of the IEEE, Piscataway, NJ, Aug. 2008, pp. 3803-3806.

*Primary Examiner* — Curtis Odom

(57) ABSTRACT

A medical system (10) and method monitor a patient. Patient data for the patient received. The patient data includes vital sign measurements and laboratory results. A vital signs instability index (VIX) regarding a physiological condition of the patient is calculated from the received vital sign measurements. A laboratory instability index (LIX) regarding the physiological condition is calculated from the received laboratory results. The VIX and the LIX are integrated into an indicator of patient deterioration.

14 Claims, 8 Drawing Sheets

METHOD OF RENDERING HEMODYNAMIC INSTABILITY INDEX INDICATOR INFORMATION

CROSS-REFERENCE TO PRIOR APPLICATIONS

This application is the U.S. National Phase application under 35 U.S.C. §371 of International Application No. PCT/IB2013/053612, filed on May 6, 2013, which claims the benefit of U.S. Provisional Application No. 61/648,838, filed on May 18, 2012. This application is hereby incorporated by reference herein.

The present application relates to clinical decision support. It finds particular application in conjunction with predicting physiological and clinical status changes and will be described with particular reference thereto. However, it is to be understood that it also finds application in other usage scenarios and is not necessarily limited to the aforementioned application.

When caring for patients, the sooner a clinician learns of deterioration of a patient, the sooner the clinician can take corrective action. This, in turn, reduces the likelihood of end organ damage, especially in the case of hemodynamic deterioration, and generally improves patient outcome. Detecting deterioration typically requires a clinician to manually review physiological data for a plurality of physiological parameters, such as systolic blood pressure, and/or laboratory data. However, clinicians care for a large number of patients and the ratio of patients to clinicians is only expected to increase. Further, the frequency with which the physiological data is generated is high. As such, clinicians are often delayed in detecting deterioration.

To alleviate this, automatic monitoring of patients is becoming increasingly prevalent. However, a principal challenge with automatic monitoring is alert fatigue. Alert fatigue is the condition in which clinicians become desensitized to clinical alerts because of the high probability that alerts are not of actual clinical significance. A simple solution is to raise alert thresholds. However, this reduces sensitivity and increases the likelihood of failing to detect patient deterioration.

Another solution is to set an inhibition period after an alert issues, so similar alerts are not issued until a rearming condition is met. In such an approach, the rearming condition is crucial to reducing the alerts. The typical rearming condition is the passing of a predetermined amount of time from the alert triggering the inhibition period and then reevaluating the physiological data after this period has passed. This is based on the notion that any alert following the first alert is likely to be based on similar physiological data, and thus does not provide any additional information to the clinician. The clinician either is already planning to take action to treat the patient if he/she agrees with the alert or doubts the validity of the alert and in either case would find another alert unnecessary. Thus it is reasonable to inhibit further alerts.

One disadvantage of this alerting solution is that additional alerts are not raised if the condition of a patient worsens within the inhibition period. Another disadvantage is the predetermined amount of time is typically fixed. As such, the predetermined amount of time is not tailored to any specific patient. Further, the predetermined amount of time does not adapt to an individual's physiologic dynamics or interventions.

Other challenges with automatic monitoring stem from predictive models typically employed by automatic monitoring systems. Such predictive models are typically trained on large databases of population data, whereby decisions using such predictive models are based on the general features of a large population. Further, differences between individuals and the general training population are typically not taken in to account. Training in this way can result in unnecessary alerts and/or failure to generate alerts for certain patients with physiological norms different from those of the general training population.

Mitigating this, direct feedback from a clinician about the validity of an issued alert can be employed for learning. However, such an approach is not possible for systems that do not have the benefit of this direct-feedback learning. Further, if an alert is issued in response to predicted events hours in advance, immediate feedback from a clinician about the validity of the alert is meaningless.

The present application provides new and improved methods and systems which overcome the above-referenced problems and others.

In accordance with one aspect, a medical system for monitoring a patient is provided. The medical system includes at least one processor programmed to receive patient data for the patient. The patient data includes vital sign measurements and laboratory results. The at least one processor is also programmed to calculate a vital signs instability index (VIX) regarding a physiological condition of the patient from the received vital sign measurements. Further, the at least one processor is programmed to calculate a laboratory instability index (LIX) regarding the physiological condition from the received laboratory results. Even more, the at least one processor is programmed to integrate the VIX and the LIX into an indicator of patient deterioration.

In accordance with another aspect, a medical method for monitoring a patient is provided. Patient data for the patient received. The patient data includes vital sign measurements and laboratory results. A vital signs instability index (VIX) regarding a physiological condition of the patient is calculated from the received vital sign measurements. A laboratory instability index (LIX) regarding the physiological condition is calculated from the received laboratory results. The VIX and the LIX are integrated into an indicator of patient deterioration.

In accordance with another aspect, a graphical user interface (GUI) for monitoring a patient is provided. The GUI includes a display of a deterioration indicator for the patient. The deterioration indicator integrates a vital signs instability index (VIX) and a laboratory instability index (LIX). The VIX and LIX indicate instability of a physiological condition of the patient. The VIX is calculated from vital sign measurement, and the LIX is calculated from laboratory results.

One advantage resides in an instability index taking into account multiple physiological parameters.

Another advantage resides in reducing alerts.

Another advantage resides in focusing a clinician's attention on patients requiring extra vigilance.

Another advantage resides in processing low-latency data separately from high-latency data.

Another advantage resides in increased sensitivity to abnormal patient conditions.

Another advantage resides in adaptability to available data.

Another advantage resides in reducing the likelihood of outlying values triggering alerts.

Another advantage resides in adjusting to cases in which a patient has conditions that are not typical of the average population.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
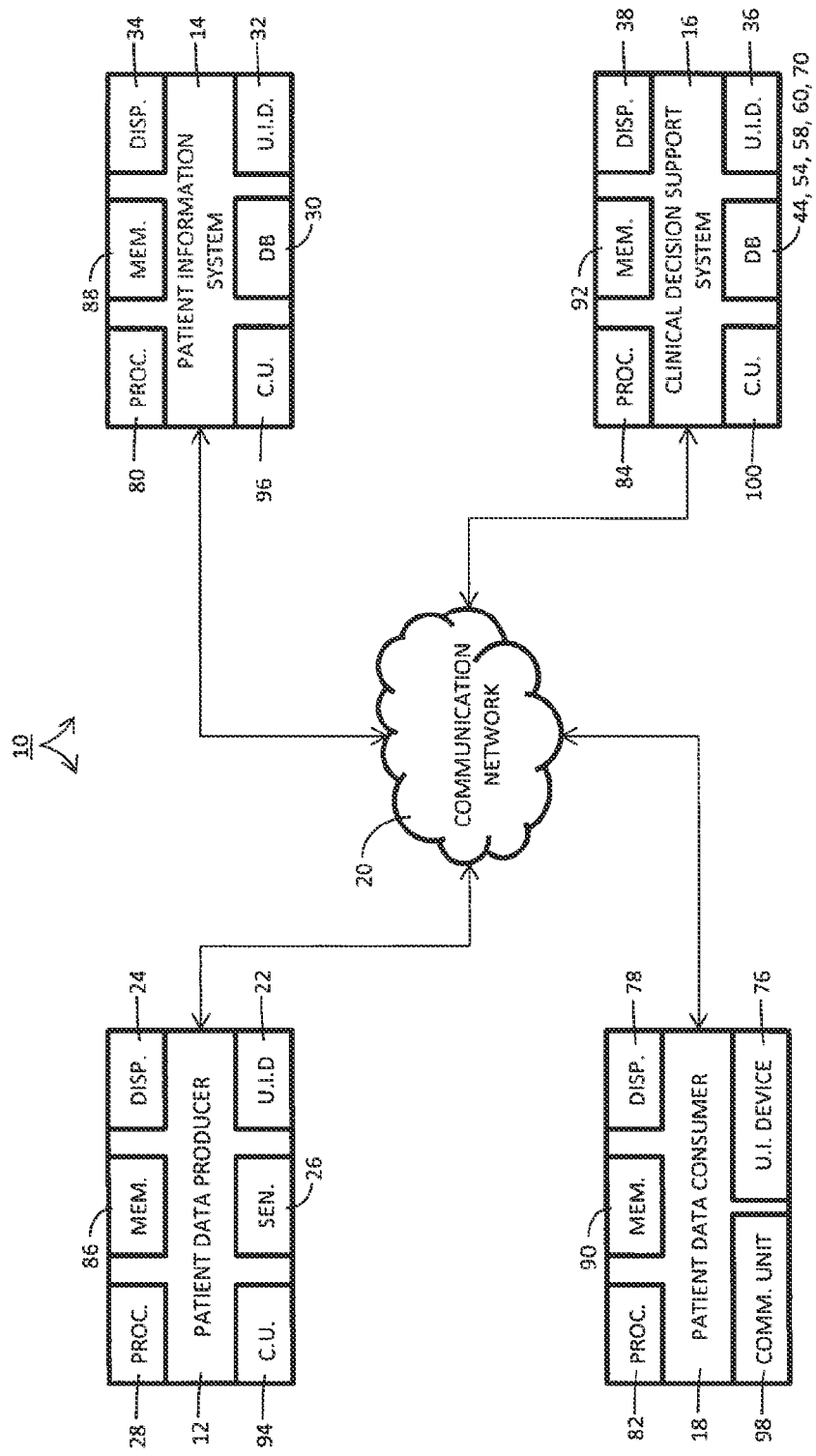
FIG. 1 is a block diagram of an information technology (IT) infrastructure of a patient care environment.
Figure 2:
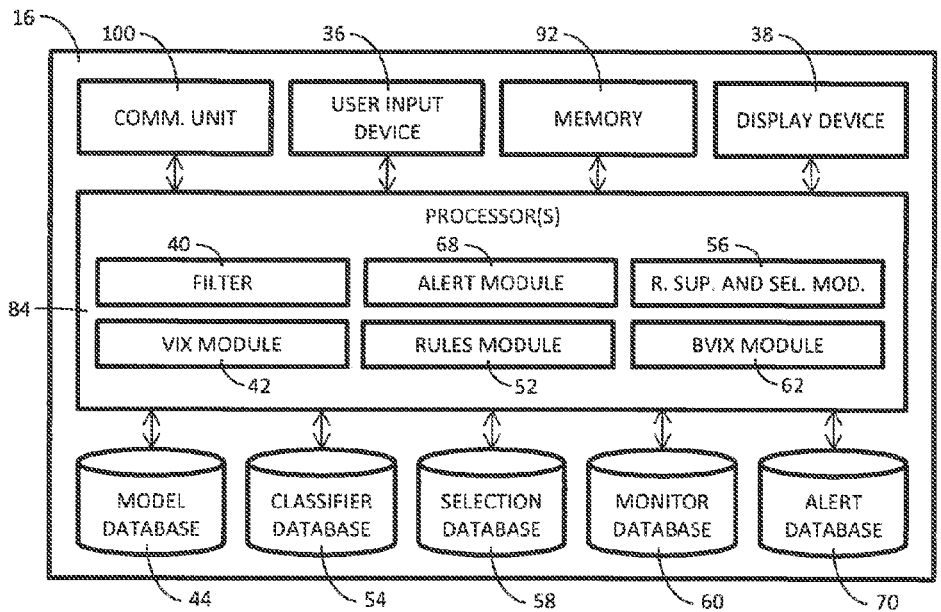
FIG. 2 is a block diagram of a clinical decision support system.

With reference to FIGS. 1 and 2, an information technology (IT) infrastructure 10 of a patient monitored environment, such as an intensive care unit (ICU), caring for one or more patients is provided. The IT infrastructure 10 includes one or more patient data producers 12, optionally a patient information system 14, a clinical decision support system (CDSS) 16, one or more patient data consumers 18, and the like. Suitably, the components of the IT infrastructure 10 are interconnected via a communication network 20, such as the Internet, a local area network, a wide area network, a wireless network, a virtual private network, or the like.

The patient data producers 12 generate patient data for corresponding patients cared for in the patient monitored environment. The patient data for a patient includes one or more of physiological data, admission, discharge and transfer (ADT) data, laboratory data, clinical data, outcome data, and alert data. Physiological data includes one or more of physiological parameter waveforms, measurements of physiological parameters typically generated at a predetermined sample rate, such as 1 second or upon a change in the parameter, observed physiological parameters, and calculated physiological parameters. Examples of such physiological parameters include systolic blood pressure (SBP), heart rate (HR), SpO2, and so on. ADT data includes values for demographic data, such as age, nationality, and so on, and care preferences, such as do not resuscitate (DNR), comfort measures only (CMO), allow natural death (AND), reason for admission to the hospital or care unit, and so on. ADT data is typically generated when a patient is admitted to and/or discharged from a medical institution and/or transferred between patient care environments, such as the ICU and/or general ward, of a medical institution. Laboratory data includes laboratory test results and is typically generated sporadically upon the happening of an event, such as a clinician ordering a lab test. Clinical data includes data indicating actions taken to improve the health of the patient and other observations such as level of consciousness, intervention measures, dialysis, medications administered, the patient social and prior medical history, history of current illness, other social or risk factors the patient possesses, such as genomics, and so on. Outcome data includes data indicating the outcome of a patient's medical treatments and/or stay in the medical institution, such as whether the patient's condition worsened or improved, whether the patient died, and so on. Typically, the outcome data is generated during the patient's stay at a medical institution after medical interventions are taken. Alert data is data indicating an alert, such as deterioration of a patient, and is typically generated in response to detection of deterioration.

The patient data can be generated manually and/or automatically, typically depending upon the type of patient data. As to the former, user input 22 can be employed. Optionally, the patient data producers 12 include display devices 24 providing users with a user interface within which to manually enter the patient data and/or for displaying patient data to clinicians. As to the latter, sensors 26, such as SpO2 sensors, measuring, for example, physiological parameters and/or lab results and/or processors 28 monitoring and/or processing data, such as patient data, can be employed. Examples of patient data producers include, but are not limited to, physiologic monitors, mobile communications devices, laboratory systems, point of care systems, clinical information systems, and so on.

The patient information system 14 stores patient data from the IT infrastructure 10, such as from the patient data producers 12 and/or the CDSS 16, in one or more databases 30 of the IT infrastructure 10. For example, the patient information system 14 can store SBP for a patient from one of the patient data producers 12. The patient information system 14 is configurable to store patient data from user input devices 32 in the databases 30 and/or to allow stored patient data to be viewed on display devices 34. The display devices 34 can also be used to facilitate receipt of data from the user input devices 32. Suitably, the patient information system 14 manually stores patient data for a predetermined amount of time, such as a year, to allow other components of the IT infrastructures 10, such as the CDSS 16, to access historical patient data. Examples of patient information systems include, but are not limited to, electronic medical record systems, departmental systems, and the like.

The CDSS 16 receives patient data for the patients from the IT infrastructure 10, such as from the patient data producers 12 and/or the patient information system 14. The CDSS can be alternatively configured so that patient data is also received from other sources, such as user input devices 36, optionally with display devices 38 providing users a user interface within which to enter the patient data, and/or sources, such as databases, external to the IT infrastructure 10. The patient data includes, for example, current patient data (e.g., current measurements of physiological parameters) and/or historical patient data (e.g., prior measurements of physiological parameters). Using the received patient data, the CDSS 16 monitors the wellbeing of the patients. Monitoring includes, for example, generating alerts when the condition of a patient appears to be deteriorating, reports summarizing the state of the patients, vital signs instability index (VIX) values, and so on.

The CDSS 16 optionally also includes a filter 40. At least some of the received patient data passes through the filter 40 that conditions patient data into a standardized format and/or filters patient data that is not suited to monitoring the wellbeing of the patients. Advantageously, conditioning patient data allows the CDSS 16 to be utilized in a variety of hosts and consume data from a variety of hosts in the native format. The filtering can include one or more of comparing the patient data to predetermined ranges of normalcy, ensuring the patient data meets time criteria for usability, and cross checking the patient data. For example, physiological data is typically filtered to remove measurements that aren't within predetermined boundaries, such as boundaries indicating possible values, and/or are otherwise highly unlikely. As another example, ADT data is typically filtered to remove ADT for patients that do not belong to a targeted demographic (e.g., age, ethnicity, etc.). For example, ADT data for a patient which has not reached a predetermined age, such as the age of majority (e.g., generally 18 in the United States), and/or which exceeds a predetermined age, such as an improbable or unlikely age. As yet another example, laboratory results are typically filtered to remove results that aren't within predetermined boundaries, such as boundaries indicating possible values, and/or which exceed a predetermined age, such as 24 hours. Advantageously, this removes data which is stale and/or likely to be outlying thereby reducing the likelihood of false alarms.

A VIX module 42 of the CDSS 16 calculates VIX values from the received patient data (as filtered, where relevant). VIX typically combines low-latency data, such as current physiological data, for a plurality of physiological parameters and, optionally, static data, such as demographic data, into a single measure reflective of stability of a physiological condition of a patient, such as the patient's hemodynamic status, pulmonary stability, nutritional stability, and so on. The CDSS 16 can be configured such that the VIX values for the patients are displayed on the display devices 38. The VIX values can be calculated continuously and/or upon the happening of an event, such as a timer event, a user input event, the availability of new data, and so on. For example, a clinician can manually trigger calculation of a VIX for a patient so as to determine the hemodynamic stability of the patient. The CDSS 16 can further be configured such that the VIX values are saved for historical analysis, typically in the patient information system 14.

A VIX value for stability of a physiological condition is calculated by providing values for predictive variables to a selected VIX model that generates the VIX value based on the predictive variables. The predictive variables are one or more of physiological parameters, features extracted from the static data, such as ethnicity, and the like relevant to determining the stability of the physiological condition. Suitably, the VIX model is selected from a plurality of VIX models in a VIX model database 44 based on the physiological condition and/or the availability of data. For example, a first VIX model is selected for stability of a first physiological condition and a second VIX model is selected for stability of a second physiological condition. As another example, a first VIX model is selected when measurements for HR and noninvasive SBP are available and a second VIX model is selected when HR and invasive SBP are available. Further, the VIX values produced by the models typically range between 0 and 1, where the closer the value is to 1, the more likely the patient is to be unstable. The VIX models can be developed using any predictive model methodology, such as logistic regression, multinomial logistic regression, linear regression and support vector machine learning.

The generic VIX models include for instance a logistic regression model for hemodynamic instability with the form of:

$$VIX = \frac{1}{1+e^{-z}}, \quad (1)$$

where $$z = \gamma + \beta_1 * SBP + \beta_2 * SI + \ldots \quad (2)$$

Specific VIX models are derived from different patient sub-populations (cardiogenic shock, hemorrhagic shock, septic shock and so on), and based on different source parameters (invasive SBP, non-invasive SBP, and the like). The model takes into account SBP and shock index (SI), which are highly significant predictive variables in determining hemodynamic stability, and returns a VIX between zero and one. SI is the ratio of heart rated divided by SBP. The higher the VIX, the less stable the patient. In some instances, $\beta_1$, the coefficient for SBP, is negative. As SBP gets lower, VIX tends to increase, reflecting that the patient is approaching a less stable state. Further, $\beta_2$, the coefficient for SI, is positive. As SI gets higher, VIX also tends to increase, again reflecting a decrease in stability. An approach for determining the coefficients is discussed hereafter.

Figure 3:
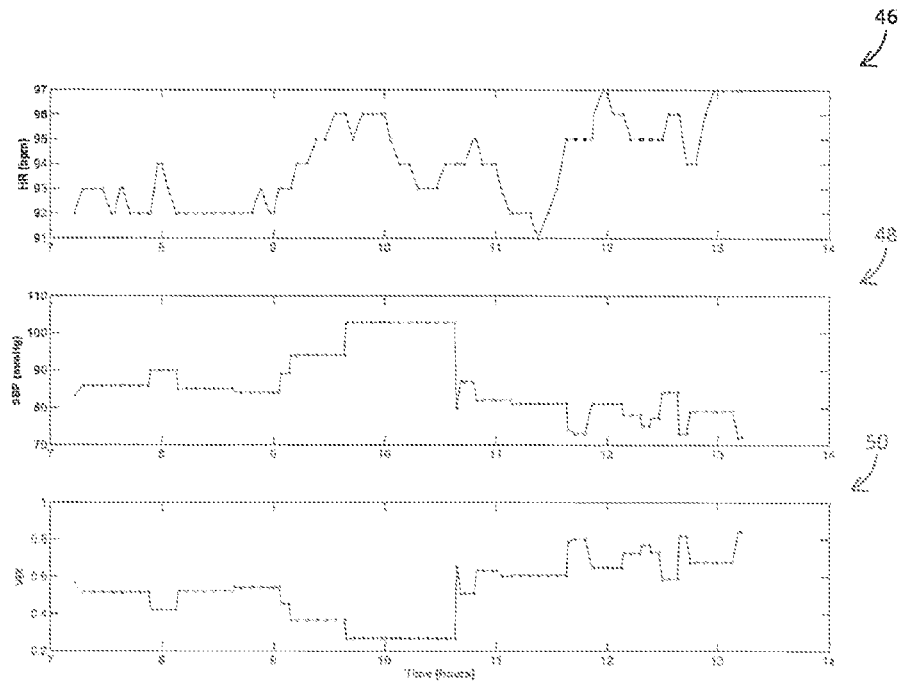
FIG. 3 is a graphical representation of a vital signs instability index (VIX) for hemodynamic stability and the corresponding inputs.

With reference to FIG. 3, a typical VIX output for hemodynamic stability and the corresponding inputs as a function of time are illustrated. The inputs were drawn from real patient data. A first panel 46 and a second panel 48 of the plot show the HR and SBP, respectively, of a patient. As noted above, HR and SBP are highly significant predictive variables in determining hemodynamic stability. In a third panel 50, the calculated VIX values are displayed. One can see that, by hour 11.75, the patient's VIX is rather high (nearly 0.8), indicating that the patient is not hemodynamically stable. Although not illustrated, at hour 14, the patient was administered a vasopressor, indicating that the hemodynamic instability was recognized by the clinician.

Referring back to FIGS. 1 and 2, the VIX module 42 can be further configured to generate and/or update the VIX models from historical patient data. The historical patient data includes records for a plurality of patients, where each records includes values for a plurality of variables, including the predictive variables, and corresponding outcome data indicating whether the patient was stable for the physiological conditions of the predictive models being updated and/or generated. Using the records, specifically the associations between the variables and the outcomes, and a predictive model methodology, such as logistic regression, multinomial logistic regression, linear regression and support vector machine learning, the predictive variables and/or one or more rules for predicting outcome are identified. For example, multivariable logistic regression can be employed to identify the predictive variables and the coefficients of the above described logistic regression model. When the VIX module 42 is employed to update the VIX models, the VIX models are typically updated in response to an event, such as a periodic timer event, a user input event, the availability of new historical patient data, and so on.

A rules module 52 of the CDSS 16, determines VIX thresholds indicating instability for the patients. A VIX threshold for a patient is determined based upon the corresponding physiological condition and, optionally, contextual data, such as laboratory data and/or demographic data. Contextual data is data describing one or more of where a patient is in the care process, the patient's problem list, interventions, demographics, laboratory tests, and the like. Contextual data is not directly relevant to the VIX, but provides an indication as to where the threshold should be set for a particular patient. For example, a patient with a creatinine value of 0.9 mg/dL may be considered stable with a VIX value of 0.5, whereas a patient with a creatinine of 3.2 mg/dL may not. When no contextual data regarding a patient is available, a generic threshold is employed for the patient. Otherwise, a threshold based on the provided contextual data is typically employed. For example, if contextual data, such as blood lab results that indicate a low hematocrit or albumin level, are generated, the VIX threshold can be adjusted to a lower value.

The VIX thresholds are suitably determined from rules of one or more VIX classifiers of a VIX classifier database 54 which discriminate between stability and instability given values for a plurality of variables, including VIX and, optionally, one or more variables of contextual data, such as laboratory tests. The rules module 52 can optionally include a VIX classifier for each possible set of input variables. For example, the rules module 52 can include a VIX classifier for an input comprised of only a VIX value and a VIX classifier for an input comprised of a VIX value and a first contextual value, such as a lab result for a particular lab test. The VIX classifiers can be generated and/or updated using any machine learning methodology, such as decision tree algorithms. Advantageously, any rule set for discriminating between stable and unstable patients using decision tree analysis will have a background rule, indicating a threshold for VIX in the absence of any contextual data. For example, if VIX is greater than 0.6, the patient is unstable. In addition to this background rule, the rule set includes rules incorporating contextual data, such as laboratory, and increasing or decreasing the VIX threshold depending upon the context. For example, if VIX is greater than 0.33 and creatinine is greater than 1.6, the patient is unstable.

In some instances, instead of rules with individual conditions based on lab results, the various lab results used in the rules could be integrated into a single laboratory instability index (LIX). Values of LIX can then be used to set VIX thresholds. Further discussion of LIX follows.

The rules module 52 may also generate and/or update the VIX classifiers from historical patient data. The historical patient data includes records for a plurality of patients, where each record includes values for input variables, including VIX and, optionally, variables of contextual data, such as laboratory tests, having a bearing on the monitoring sensitivity for the patient, and outcome data indicating whether the patient was unstable. Using the records, specifically the associations between the input variables and the outcomes, and a machine learning algorithm, such as a decision tree algorithm, one or more rules for determining the outcome are determined. When the rules module 52 is employed to update the classifiers, the VIX classifiers are typically updated in response to an event, such as a periodic timer event, a user input event, the availability of new historical patient data, and so on.

A rule supervisor and selector module 56 determines a set of one or more monitoring rules and/or one or more VIX models to employ for each patient to be monitored. A monitoring rule takes as input values for one or more variables, such as a physiological parameter, and provides an indication as to whether a patient is deteriorating. To determine a set of one or more monitoring rules and/or one or more VIX models, one or more selection rules of a selection rules database 58 are employed. The selection rules select one or more monitoring rules from a plurality of monitoring rules in a rules monitoring database 60 and/or select one or more VIX models from the VIX database 44. The monitoring rules are suitably generated manually by, for example, a clinical expert and/or automatically using a machine learning algorithm.

The selection rules can be based upon one or more of available patient data, patient context, and/or the source of the patient data. Typically, however, the selection rules are based upon contextual data, such as laboratory data and/or demographic data. Where contextual data is available, the selection rules determine a set of monitoring rules and/or VIX models tailored to the available contextual data. Where contextual data is unavailable, the selection rules return a generic set of monitoring rules and/or a generic VIX model selection. In this way, the rule supervisor and selector module 56 is adaptive to available patient data. While selection rules based on contextual data are typical, other selection schemes are contemplated. For example, it is contemplated that the rule supervisor and module 56 simply returns a set of monitoring rules for every patient regardless of the availability of contextual data. Similar to the monitoring rules, the selection rules are suitably generated manually by, for example, a clinical expert and/or automatically using a machine learning algorithm.

The monitoring rules may be based on VIX values. However, one challenge with employing VIX values is that a high VIX value can be the result of outlying physiological data due to, for example, a misplaced monitoring lead or a patient's sudden change in arm position, or movement from a prone to a sitting or standing position. Especially where automatic patient monitoring is employed, such data can lead to false alerts. To reduce the likelihood of these false alerts, a baseline VIX (bVIX) indicating how the VIX has been behaving is calculated by a bVIX module 62 of the CDSS 16. The bVIX module 62 calculates bVIX values from historical patient data. Many methods can be used to estimate the trend in a series of VIX values. Some are more sophisticated than others. In one example, the bVIX value is the maximum VIX value or the 90 percentile value within the past predetermined amount of time, such as three hours.

When a bVIX is employed, an alert exceeding a trigger threshold is indicated only if a bVIX indicates a rising trend in VIX. Then the current high VIX value is more likely to reflect the true state of the physiological condition. Otherwise a false alert is more likely. In one example, a rising trend is detected when the current VIX value is more than a predetermined threshold and bVIX is at least some fraction of the threshold (e.g., ¾ or ⅔). This means the current VIX is high enough to cause alarm and an earlier VIX value is already quite high. Then and only then is an alert raised. If bVIX is too low, then the current VIX, though high, is more likely to be an aberration and no alarm is raised. This specific implementation has the advantage of being simple and efficient and has proved to be effective in reducing alerts due to data outliers.

Figure 4:
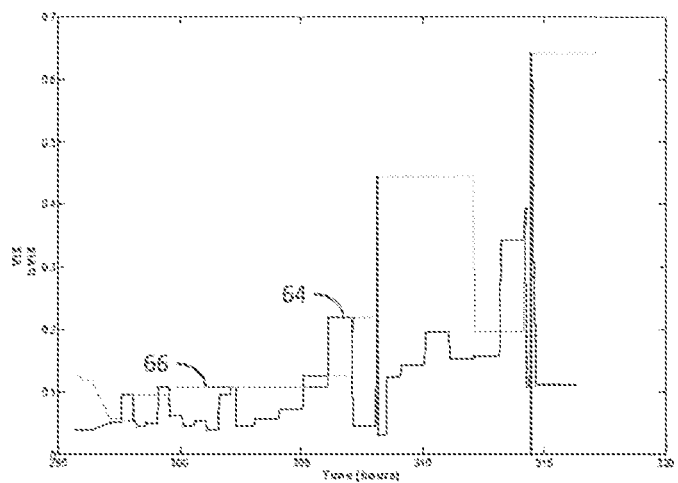
FIG. 4 is a graphical representation of a baseline VIX and a vital signs instability index.

With reference to FIG. 4, an example of VIX values 64 and the corresponding bVIX values 66 calculated for a patient during a portion of their stay in the patient care environment as a function of time since admission is provided. With reference to around hour 308, the patient's VIX value reaches a high enough value to trigger an alert. However, because the bVIX value at this point in time (~0.22) is too low, no alarm is triggered as a result of this spike in VIX. In this way, the implementation of bVIX has made it impossible to trigger an alert due to this quite possibly aberrational data. Later in the patient's stay, around hour 314.5, the patient's VIX again becomes high enough to cross a threshold for instability. This time, however, the bVIX is also high enough (~0.4) to allow an alarm to be triggered. Essentially, bVIX is sensitive to trends in data; a high VIX resulting from a gradual increase in VIX values is far more likely a result of actual important physiological changes than is a VIX that suddenly increases.

Referring back to FIGS. 1 and 2, an alert supervisor module 68 monitors the patient data for the patients and generates alerts when deterioration is detected. To determine when a patient is deteriorating, the alert supervisor module 68 employs the set of monitoring rules for the patient determined by the rule supervisor and selector module 56. As noted above, the monitoring rules take as input values for one or more variables, such as physiological parameters, typically received from the IT infrastructure 10. Further, the input variables can include VIX. The VIX values are received from, for example, the VIX module 42 and generated, for example, according to the VIX model selections made by the rule supervisor and selector module 56. Further, the thresholds for the monitoring rules for the VIX values are received from the rules module 52.

When it is determined that a patient is deteriorating, an alert to that affect is generated. The alert is suitably generated and addressed to a clinician according to one or more rules in an alert rules database 70. The rules can take into account one or more of hospital policy, clinician worklists, on-call status of clinicians, clinician preferences, and so on. For example, suppose hospital policy specifies that in response to an alert of a particular type, alert the on-call physician overseeing the physician. Further, suppose the on-call physician wishes to be contacted in a particular way, such as text message. The rules can be employed to generate and send an alert meeting these requirements. Alert escalation is also contemplated. Alert escalation is the idea of escalating an alert by resending it to the same or a different clinician after conditions, such as the passing of a predetermined amount of time without receiving an acknowledgment, are met.

In addition to sending the alert, alerts for the same deterioration are disarmed (i.e., prohibited from being triggered) until a rearming condition is met. The rearming conditions can include, for example, the passage of a predetermined amount of time. Further, the rearming conditions can, for example, be determined by an adaptive rearming method. The adaptive method presupposes familiarity with the typical intervention measures taken by clinicians in response to deterioration of the physiological condition corresponding to the disarmed alert and the availability of clinical data indicating interventions taken by clinicians. Further, the adaptive method presupposes an index or parameter that reflects a patient's stability with regard to the physiological condition. For example, when the physiological condition is hemodynamic stability, the index or parameter can be VIX and typical intervention measures include the administration of fluids, vasopressors, or packed red blood cells.

According to the adaptive method, if an alert for deterioration of a physiological condition is issued, alerts for the same deterioration are prohibited from being issued for a predetermined amount of time, such as three hours. The predetermined amount of time corresponds to the lead time of the prediction that deterioration will occur and typically varies depending on the physiological condition. After the predetermined amount of time has passed, a determination is made as to whether intervention measures have been taken to address the deterioration based on clinical data typically received from the IT infrastructure 10 and knowledge of typical intervention measures for the physiological condition.

If no intervention has been or is being administered, alerts for the same deterioration are disarmed unless and/or until the index or parameter has worsened by a threshold amount compared to the index or parameter value at the time of the initial alert. The threshold amount can be fixed or variable, such as half of the distance to a previous index or parameter value. By rearming in this way, the lack of intervention by a clinician after a significant time has passed is interpreted as an indication that the patient's condition at the time of the first alert is acceptable for that particular patient. Therefore, even though the index or parameter is abnormal, or unstable, by population standards, the adaptive method learns that it is normal. If intervention is being administered, this is recognized as acknowledgement by clinicians and further alerts are unnecessary. After the intervention has ended, alerts for deterioration of the physiological condition are rearmed after a predetermined amount of time passes.

Figure 5:
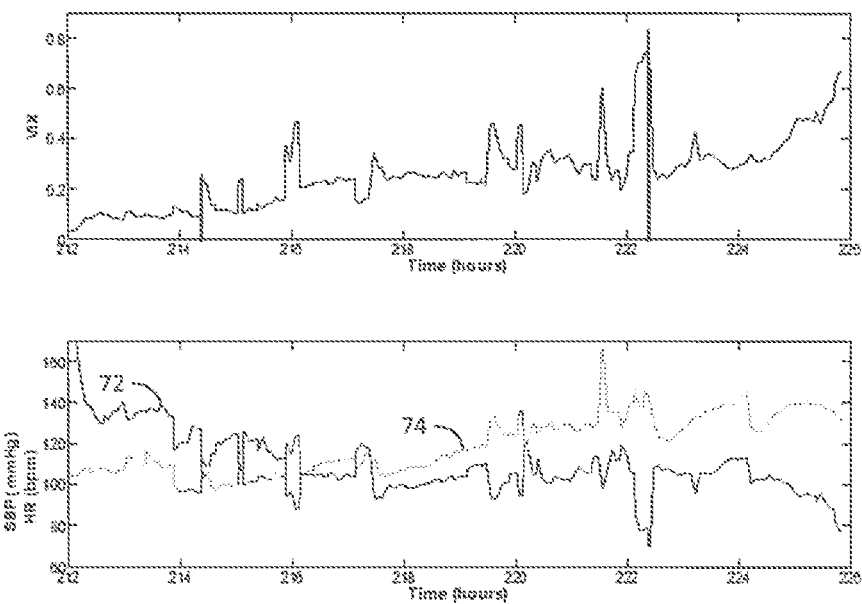
FIG. 5 is a graphical representation of a VIX for hemodynamic stability and the corresponding inputs.

With reference to FIG. 5, a plot of the VIX for a patient and the corresponding inputs, SBP 72 and HR 74, over the course of several hours is illustrated. An alert is generated at hour 214.5 as the VIX value of the patient crosses the alert threshold. During the course of the three hours that follows the first alert, no intervention is taken. This is interpreted to mean that the patient's dynamics at the time of the first alert are acceptable for that particular patient. Therefore, after three hours have passed, no alert is generated because the patient's VIX is not much higher than it was at the time of the first alert. By the time hour 222.5 is reached, however, VIX has significantly increased and, therefore another alert is issued for the patient. It should be noted that at hour 226, the clinician administered vasopressor indicating that, indeed, the patient experienced a clinically notable incident of hemodynamic instability.

Referring back to FIGS. 1 and 2, the patient data consumers 18 consume patient data from the IT infrastructure 10, such as from the patient data producers 12, the CDSS 16, the patient information system 14, and so on, for the patients. For example, the patient data consumers 18 can receive VIX values from the CDSS 16. As another example, the patient data consumers 18 can receive respiration rate and heart rate from the patient data producers 12. As yet another example, the patient data consumers 18 can receive alerts from the CDSS 16. Optionally, the patient data consumers 18 also receive patient data from user input devices 76, optionally with display devices 78 providing users a user interface within which to enter the patient data. Examples of patient data consumers include, but are not limited to, patient monitors, spot check patient monitors, mobile communications devices, patient information systems, clinical decision support systems, and so on.

Consumption can include processing the received patient data to generate additional patient data and/or consolidating the patient data into reports. A report is a computer file in a format, such as PDF, DOCX, DOC, and so on. Optionally, newly generated patient data and/or newly generated reports are saved in the IT infrastructure 10, such as in the patient information system 14. Further, optionally, newly generated reports are electronically messaged to clinicians using, for example, email and/or printed using, for example, a laser printer, an inkjet printer, and so on. Consumption can also include displaying the received patient data, such as alerts or VIX values, for at least one patient on a user interface presented to clinicians via the display devices 78. The user interface is typically continuously updated as patient data is received. Advantageously, this allows clinicians to monitor patients in near real time.

When displaying patient data and/or generating a report, the report and/or display suitably includes at least patient name and VIX values for at least one patient. Where the received patient data includes patient data for a plurality of patients, the received patient data is suitably formatted in a table structure with a plurality of rows corresponding to the patients. The rows can optionally be sorted and/or can be sorted by severity of VIX. For example, a clinician can employ the user input devices 76 to sort a table of patient data based on VIX. Further, clinicians can optionally selectively view the details of a VIX. For example, a clinician can employ the user input devices 76 to select a VIX for a patient and view the variables and respective values that yielded the VIX, optionally ranked based on contribution. Even more, the patient data can optionally be grouped based on similar VIXs. Groups include, for example, one or more of very low risk, low risk, moderate risk, high risk, and so on.

A VIX can be represented as one or more of textual values (e.g., scores, probabilities, and so on), icons (e.g., one or more of shape, color, background, and so on based on severity), a combination of the foregoing, and so on in a user interface and/or a report. For example, a VIX can be represented as a circle having a background color dependent upon severity, such as red for high risk, yellow for medium risk, and green for low risk. An icon can further includes a textual value overlaid thereon, optionally depending upon severity. For example, an icon can include a probability overlaid thereon when the severity is medium. A VIX can also be presented to the use as a discrete message (e.g., alert, text page, email, SMS, and so on) or as a parameter based on the absolute probability that the patient will have an instability event in a preconfigured or continuous time horizons, or as a normalized scale of overall prediction of instability based on VIX and other CDSS algorithms running for the patient.

The components of the IT infrastructure 10 suitably include processors 28, 80, 82, 84 executing computer executable instructions embodying the foregoing functionality, where the computer executable instructions are stored on memories 86, 88, 90, 92 associated with the processors 28, 80, 82, 84. The processor(s) 84 of the CDSS 16, for example, execute computer instructions on the one or more memories 92 of the CDSS 16 embodying the functionality of one or more of the filter 40, the VIX module 42, alert module 68, the rules module 52, the rule supervisor and selector module 56 and the bVIX module 62. It is, however, contemplated that at least some of the foregoing functionality can be implemented in hardware without the use of processors. For example, analog circuitry can be employed. Further, the components of the IT infrastructure 10 include communication units 94, 96, 98, 100 providing the processors 28, 80, 82, 84 an interface from which to communicate over the communication network 20. Even more, although the foregoing components of the IT infrastructure 10 were discretely described, it is to be appreciated that the components can be combined. For example, the patient data consumers 12 and the patient data producers 18 can be the same and/or have overlap. As another example, the CDSS 16 can be integrated with the patient data consumers 18 and/or the patient data producers 12. As yet another example, the CDSS 16, the patient data consumers 18 and the patient data producers 12 can be combined into a standalone device independent from the communication network 20.

Figure 6:
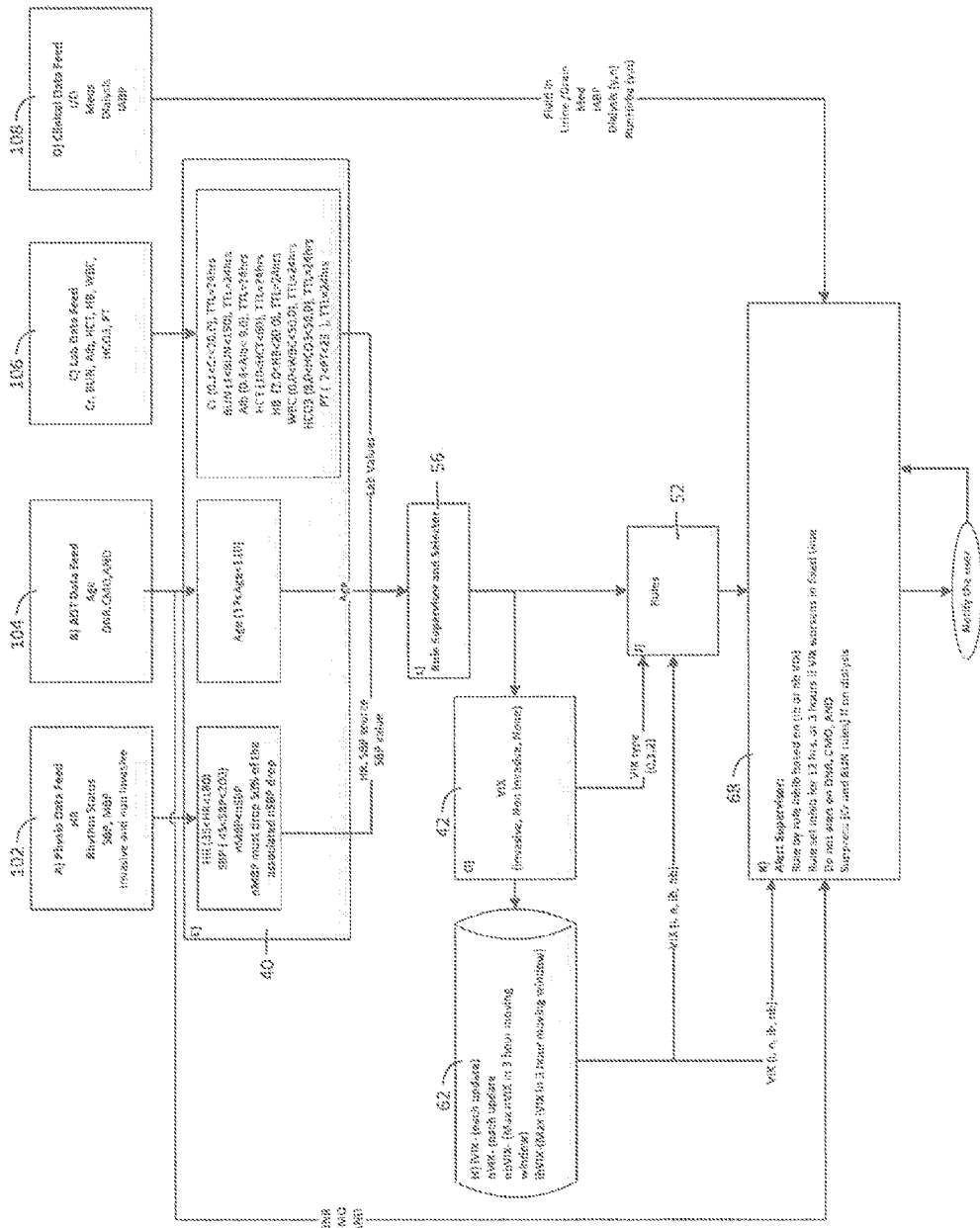
FIG. 6 is a flow chart of a clinical decision support system.

With reference to FIG. 6, a flow chart illustrating operation of the CDSS 16 according to one embodiment thereof. The CDSS 16 receives patient data from a physiological data feed 102, an ADT data feed 104, a laboratory data feed 106, and a clinical data feed 108. As illustrated, the physiological feed 102 provides measurements for HR, SBP (invasive and/or noninvasive), mean blood pressure (MBP) (invasive and/or noninvasive), and heart rhythm status; the ADT data feed 104 provides a patient's age, whether a patient does not want to be resuscitated, whether a patient wants comfort measures only, and whether a patient wants to allow a natural death; the laboratory data feed 106 provides lab results for blood tests, including tests for creatinine (Cr), blood urea nitrogen (BUN), albumin (Alb), hematocrit (HCT), hemoglobin (HB), white blood cell (WBC) count, bicarbonate (HCO3), and prothrombin time (PT); and the clinical data feed 108 describes medications (Meds) provided to a patient, whether the patient is administered dialysis, whether a patient has a intraaortic balloon pump (IABP), any other drugs and the like administered to a patient and any samples drawn from a patient. Typically, the data feeds 102,104,106,108 are the patient data producers 12.

At least some of the patient data, including physiological data, ADT data and laboratory data, passes through the filter 40. The filter 40 standardizes the format of the data and/or ensures the HR and SBP are within possible ranges, e.g., noninvasive MBP is less than noninvasive SBP, and the noninvasive MBP drops 50% of the associated noninvasive SBP drop. Further, the filter 40 ensures the patient age is reasonable and exceeds a predetermined age, such as the age of majority (e.g., generally 18 in the United States). Even more, the filter 40 ensures Cr, BUN, Alb, HCT, HB, WBC, HCO3 and PT are within possible ranges and the tests were performed within 24 hours (i.e., the time to live (TTL) of laboratory tests is only 24 hours).

The filtered patient data passes to the rule supervisor and selector module 56 where it is used by the rule supervisor and selector module 56 to determine a set of one or more monitoring rules and/or one or more VIX models to employ for each patient to be monitored. As illustrated, the available VIX models include a noninvasive model and an invasive model. The patient data is used to provide a context for the patient and based on this context, the appropriate monitoring rules and VIX model(s) are selected. The determination of VIX models passes to the VIX module 42, which calculates VIX values from the filtered patient data using the selected VIX model(s). The VIX values calculated by the VIX module 42 pass to the bVIX module 62, which calculates bVIX values from the VIX values using a three hour moving window. The determined set of monitoring rules passes to the rules module 52, which determines thresholds for the VIX values.

The alert supervisor module 68 receives the rules and thresholds, as well as the VIX and bVIX values, and monitors for patient deterioration through application of the rule set. Upon determining deterioration, the alert supervisor 68 notifies users of patient deterioration and disarms alerts for the same deterioration. As illustrated, alerts are rearmed after 12 hours pass or 3 hours if VIX worsens. Further, the monitoring rules do not alert if the patient is DNR, CMO, or AND and/or CR and BUN rules are suppressed if the patient is on dialysis. The alert supervisor module 68 also has the ability to receive feedback from the user via the CDSS 16 regarding the user's desired alert behavior. In the case, the CDSS 16 is deployed where there is no connection to interventions charted in the patient information system 14, the user has the ability to indicate that an intervention is planned, thus suppressing new alerts until the user indicates the intervention is complete or the condition worsens to a new threshold that is based on the first alert and type of intervention indicated by the user.

The foregoing dealt with the generation of alerts indicating patient deterioration based on VIX. However, one challenge with alerts is that alerts aren't always user friendly. Alerts can prove to be an annoyance to clinicians caring for patients and can provide clinicians with an information overload. To alleviate these challenges with alerts, an indicator indicating patient deterioration can be used in lieu of alerts.

The deterioration indicator is driven by one of two versions of VIX, nVIX and iVIX. The specific version of VIX depends on whether it is calculated noninvasively or invasively. For example, when VIX is used for hemodynamic stability, nVIX can be VIX determined using noninvasive BP and iVIX can be VIX determined using invasive BP. VIX can be determined as described above in connection with the VIX module 42 of FIG. 2. One challenge with the deterioration indicator is that lab values cannot be used as they were with deterioration alerts to set VIX thresholds for alerting. Instead, lab values are used to create an instability index of a physiological condition based on only lab values, hereafter referred to as a laboratory instability index (LIX). Such a physiological condition can include the patient's hemodynamic status, pulmonary stability, nutritional stability, and so on.

LIX values are suitably determined in the same manner as VIX values, except that LIX values are calculated from only lab data. Namely, a LIX value is calculated by providing values for predictive variables to a selected LIX model that generates the LIX value based on the predictive variables. The predictive variables are one or more features extracted from lab data and which are predictive of instability on the physiological condition. LIX is typically based on logistic regression (e.g., a model of the same form as the model of Equation 1), but other models are contemplated.

Like VIX, LIX includes two versions, nLIX and iLIX. The version of LIX used to determine the deterioration indicator depends upon the version of VIX used to determine the deterioration indicator. Where nVIX is used, nLIX is used, and where iVIX is used, iLIX is used. For example, where LIX represents hemodynamic instability, nLIX is for a patient with noninvasive BP and iLIX is for a patient with invasive BP. Both versions of LIX use only lab values, but the lab values and the model parameters (e.g., logistic regression coefficients) that work best are somewhat different for patient episodes depending upon which version of LIX is being used. For example, where LIX represents hemodynamic instability and is used with a logistic regression model, the lab values and the weighting that work best vary depending upon whether BP is measured invasively or noninvasively. Continuing with this example, LIX typically depends on albumin, BUN, and white blood cell count for noninvasively monitored patients, and LIX typically depends on the same set of labs with the addition of HCO3 for invasively monitored patients.

If a value for a lab parameter is missing that goes into the LIX calculation, it is assumed that the patient has an average value for that lab parameter, the average value shared by a patient population to which the patient belongs. A value for a lab parameter could be missing, for example, because it has not been measured yet. Further, a sample-and-hold scheme is typical used with no time limitations for lab parameters used by the LIX calculating. In a sample-and-hold scheme, a value for a lab parameter is typically used until replaced with a newer value. In some instances, varying schemes can be used depending upon the lab parameter. For example, a sample-and-hold scheme could only be used for HCO3 so long as the most recent value is no older than a predetermined period of time, such as 3 hours. Otherwise, an average value shared by a patient population to which the patient belongs can be used. For most lab parameters, a sample-and-hold scheme can be used for a parameter so long as the current value is no older than a time between 12 and 36 hours. Thus, there is a nLIX value and an iLIX value at all times for a patient.

Both nLIX and iLIX are divided into a plurality of bands, typically three bands: a low risk band; a medium risk band; and a high risk band. At any point in time, a patient's deterioration indicator is based on the patient's VIX value and the LIX band that the corresponding LIX value falls into. The deterioration indicator is determined by using a VIX-to-prevalence table which has rows corresponding to VIX values and columns corresponding to the plurality of bands for both nVIX and iVIX. For example, the VIX-to-prevalence table can include 100 rows corresponding to 100 possible VIX values in 0.01 increments and 6 columns corresponding to six LIX bands, including a low, medium and high risk band for each of nLIX and iLIX.

Figure 7:
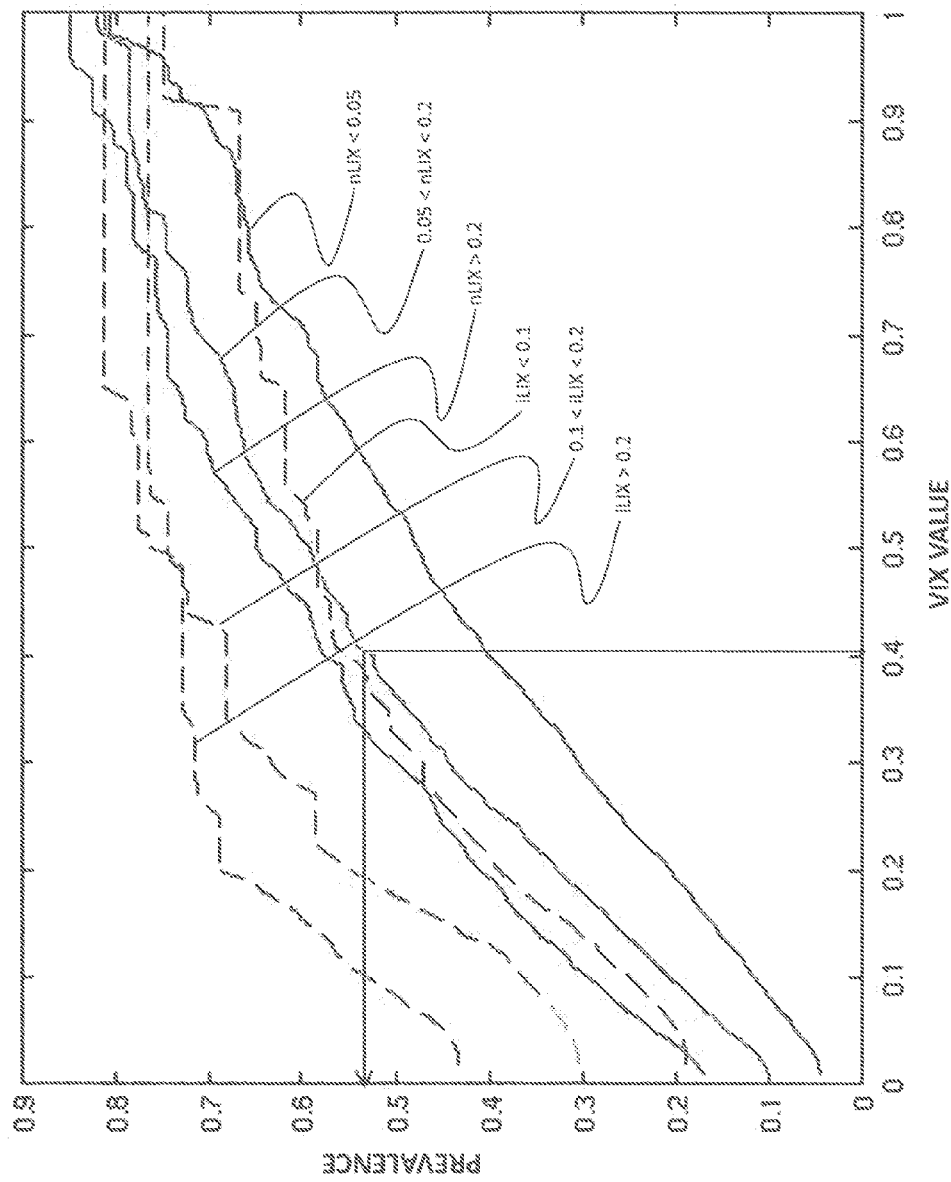
FIG. 7 is a graphical illustration of the lookup of a prevalence value using a vital signs instability index and a laboratory instability index.

To lookup a prevalence value, a row in the VIX-to-prevalence table is determined by matching a VIX value to a corresponding row of the VIX-to-prevalence table. For example, drawing from the above example, this can be performed by determining an index identifying a row of the VIX-to-prevalence table. The index can be determined according to the following equation: round(100*VIX+0.5), where the round function rounds up or down. As should be appreciated, VIX values range from 0 to 1. With reference to FIG. 7, the lookup is graphically shown, where the vertical axis corresponds to prevalence, the horizontal axis corresponds to VIX, and each line corresponds to a LIX band. As illustrated, a noninvasively monitored patient with a VIX value of 0.4 and an nLIX value in a medium risk range is shown to have a prevalence of about 0.54.

The VIX-to-prevalence table can be determined using a population of stable VIX segments, and unstable VIX segments one hour prior to receiving drugs affecting the stability. For example, when VIX corresponds to hemodynamic stability, the drugs can correspond to pressor and/or inotropic drug. The stable and unstable segments correspond to VIX trends over a predetermined period of time, typically 3 hours. The population can be divided into subpopulations corresponding to the LIX bands. For each of the subpopulations (e.g., six subpopulations according to the above example), the fraction of unstable segments to all segments (i.e., prevalence) is calculated for different VIX ranges (e.g., in 0.01 increments). After some smoothing, these prevalence values can be added to the VIX-to-prevalence table.

It should be noted that the prevalence values represented in the table are based on the specific population used to calculate them and need not represent the prevalence values of the targeted population. Rather, the purpose of the population is to map various VIX values under different circumstances (i.e., noninvasive versus invasive LIX values and different LIX value ranges) to a unified index.

A prevalence value can be mapped to a final indicator value, typically between 0 and 100, via the equation:

$$\text{indicator} = \frac{\text{prevelence} - \alpha}{\beta - \alpha} * 100, \quad (3)$$

where $\beta$ is the maximum prevalance value in the VIX-to-prevalence table, and $\alpha$ is the minimum prevalance value in the VIX-to-prevalence table. According to the VIX-to-prevalence table used for FIG. 7, β is 0.8500 and α is 0.0422. Hence, a prevalence value can be mapped into the final indicator by linearly adjusting the values so that they scale over the desired range.

After determining the final indicator, the final indicator can be displayed to a clinician. The final indicator indicates the risk of patient deterioration, with higher values indicating a higher risk of patient deterioration. The final indicator can be directly or indirectly displayed to a clinician. As to the former, for example, the final value can be displayed to a clinician using text, a bar chart, or the like. As to the latter, for example, the range of indicator values can be divided into bands corresponding to the risk of patient deterioration. For example, the range of indicator values can be divided into thirds corresponding to low, medium and high risk of patient deterioration. The final indicator can then be mapped to one of these bands and the band can be identified to a clinician. The band is typically identified to a clinician using colors. For example, drawing on the foregoing example, red can indicate a high risk of patient deterioration, yellow can indicate a medium risk of patient denervation and green and indicate low risk of patient deterioration.

Two complications regarding the deterioration indicator pertain to baseline filtering and re-arming. Deterioration alerts used a baseline of maximum VIX values over a preceding period to filter VIX outliers. These were incorporated into rules which set the VIX thresholds. However, deterioration indictors are calculated for each VIX value, so this filtering has to be done to all the VIX values. In other words, the VIX values used in the VIX-to-prevalence table are filtered by the baseline.

The baseline filtering can be done by calculating the baseline VIX, bVIX, for both nVIX and iVIX to produce a nbVIX and a ibVIX. The bVIX can be the maximum VIX value, or a percentile, such as 90 percentile, over a previous period of time (e.g., the three preceding hours). After calculating the bVIX values, each VIX value is compared to its corresponding bVIX, and if it exceeds the bVIX by a specified proportion, then it is suppressed. However, the suppressed VIX value goes into the calculation of the bVIX for the next value of VIX. For example, a VIX value can be suppressed if the following equation is met: bVIX<=0.7*VIX (i.e., VIX>=(10/7)*bVIX). If a VIX value is not suppressed, the VIX value is used to determine a deterioration indicator.

When VIX is used only for deterioration alerts, outliers at the low end of the range are not a concern. However, when VIX is used for a deterioration indicator, such outliers are a concern. In order to address these outliers, a second baseline VIX, lo_bVIX, is calculated. The lo_bVIX can be the minimum VIX value, or a percentile, such as 10 percentile, over a previous period of time (e.g., the three preceding hours). Each new VIX value is compared to its corresponding lo_bVIX and suppressed if it is less than the lo_bVIX by a specified proportion. The suppressed VIX value goes into the calculation of the lo_bVIX for the next value of VIX. For example, a VIX value can be suppressed if the following equation is met: VIX<=0.8*lo_bVIX. In view of the foregoing, there are two baselines, an upper and lower one, used to filter possible VIX outliers. All VIX values hereafter referred to are filtered VIX values.

Regarding re-arming, this is not an issue, strictly speaking, since re-arming concerns alerting. However, if the deterioration indicator is going to be tested in a clinical setting, performance statistics, such as positive predictive value (PPV), are needed, as well as criteria defining when a deterioration indicator value is to be counted as a positive. One way to determine whether deterioration indicator values are positive is to generate alerts. One way to generate alerts is to generate alerts when deterioration indicator values exceed an alert threshold. However, as with deterioration alerts, alerts will continuously sound for some patients for this approach. This will be annoying to clinicians if the patient is stable. Further, it will be annoying if the patient is unstable, since once the clinician has been alerted, subsequent alerts are likely to be perceived as annoying.

The deterioration alerts used a dynamic re-arming mechanism so that alerts were not re-issued unless the patient's condition was seriously deteriorating. The re-arming scheme used for the deterioration alerts can be adapted for use with the deterioration indicator. It's expected that it will not only be useful for measuring performance in a clinical study, but also for highlighting the deterioration indicator when the patient's condition is deteriorating. For example, an icon representing the deterioration indicator could be highlighted (e.g., with a contrasting border or frame) when the patient's deterioration indicator has deteriorated significantly. The following method focuses on re-arming for alerts, but can be applied to highlighting.

In designing the re-arming method, a determination was made as to whether the re-arming method should apply to VIX or to the determination indicator. Initially, it might seem natural to apply the re-arming method to the deterioration indicator rather than some component that goes into the deterioration indicator (e.g., VIX). However, consider the following scenario pertaining to hemodynamic instability. A clinician switches the patient from noninvasive to invasive BP. Since patients whose BP is being measured invasively tend to be more unstable, the deterioration indicator will almost certainly worsen. However, there is a high likelihood that the clinician put the patient on an arterial line (i.e., A-line) because of concern about this patient and wanted more intense monitoring. Hence, an alert based on the deteriorating deterioration indicator isn't telling the clinician anything new. More generally, since many of the elements (as represented by the six columns of the VIX-to-Prevalence table) that go into the deterioration indicator change slowly, it is important that any alerts based on the deterioration indicator draw attention to rapid changes in the underlying VIX values. To present one more scenario, a patient's deterioration indicator may improve because a new lab value has just come in that was better than before, moving the patient into a lower risk LIX band, but at the same time the VIX score may be deteriorating. By basing the alerts on VIX, this deteriorating situation will be brought to the attention of the clinician.

The re-arming method used by the deterioration indicator is similar to that used by the deterioration alerts. Namely, static re-arming is the same. If intervention information is available, re-arming can be suppressed during the intervention and a follow-up inhibition period, and then reset. Dynamic re-arming is also similar.

With deterioration alerts, subsequent alerts typically issue only if the patient's VIX has worsened significantly since the last alert. With the deterioration indicator, since there are no alerts, a maximum VIX value (i.e., max_vix) is stored. This is done separately for nVIX and iVIX. Initially, the max_vix is the initial VIX value. If VIX surpasses either of two thresholds, then max_vix is set to the current VIX value, and VIX is marked as a potential deterioration indicator alert value. These two thresholds include: (1) max_vix+vix_thr; and (2) (max_vix+1.0)/2, where vix_thr is a constant, typically 0.2, representing an amount above the max_vix that indicates potential deterioration. The second threshold is equivalent to saying VIX is greater than half way between max_vix and the maximum possible VIX of 1.0. The second condition will become operative once 1.0-max_vix is less than 2*vix_thr.

In effect, the foregoing procedure returns a list of potential VIX values that may become alerts, typically in increasing order. The max_vix can also be set to the current VIX value if the current VIX value is less than lo_vix_thr*max_vix, where lo_vix_thr is a threshold indicating potential deterioration. By setting lo_vix_thr to 0.05, for example, if VIX drops to below 5% of max_vix, max_vix is reset to the current VIX value. This additional approach to setting max_vix should be used if intervention information is not available, since the deterioration indicator should be re-armed if the patient has an intervention and then re-stabilizes.

The list items of the list of potential VIX values that are too close to each other are eliminated. In other words, a refractory period (e.g., 3 hours) is applied to the list items to remote items within the refractory period of each other. After eliminating list items that are too close, the list items are separated by at least the refractory period. These remaining values can then be used for alerting (at least for evaluation purposes), provided they are above a specified threshold indicating when alerts should be generated. As noted above, these remaining values can also be used for highlighting a displayed deterioration indicator, for example, by framing, provided they are above a specified threshold.

As can be seen, the re-arming method is controlled by max_vix, marking VIX values that are higher than max_vix (by some threshold) and re-setting max_vix to the current value of VIX. If the second mechanism is enabled, max_vix is re-set to the current VIX if the current VIX drops to a specified fraction of max_vix. It should be stressed that the re-arming method is for marking VIX values as potential alerts (or highlighted deterioration indicator values), once they have been converted into deterioration indicator values via the VIX-to-prevalence table.

Figure 8:
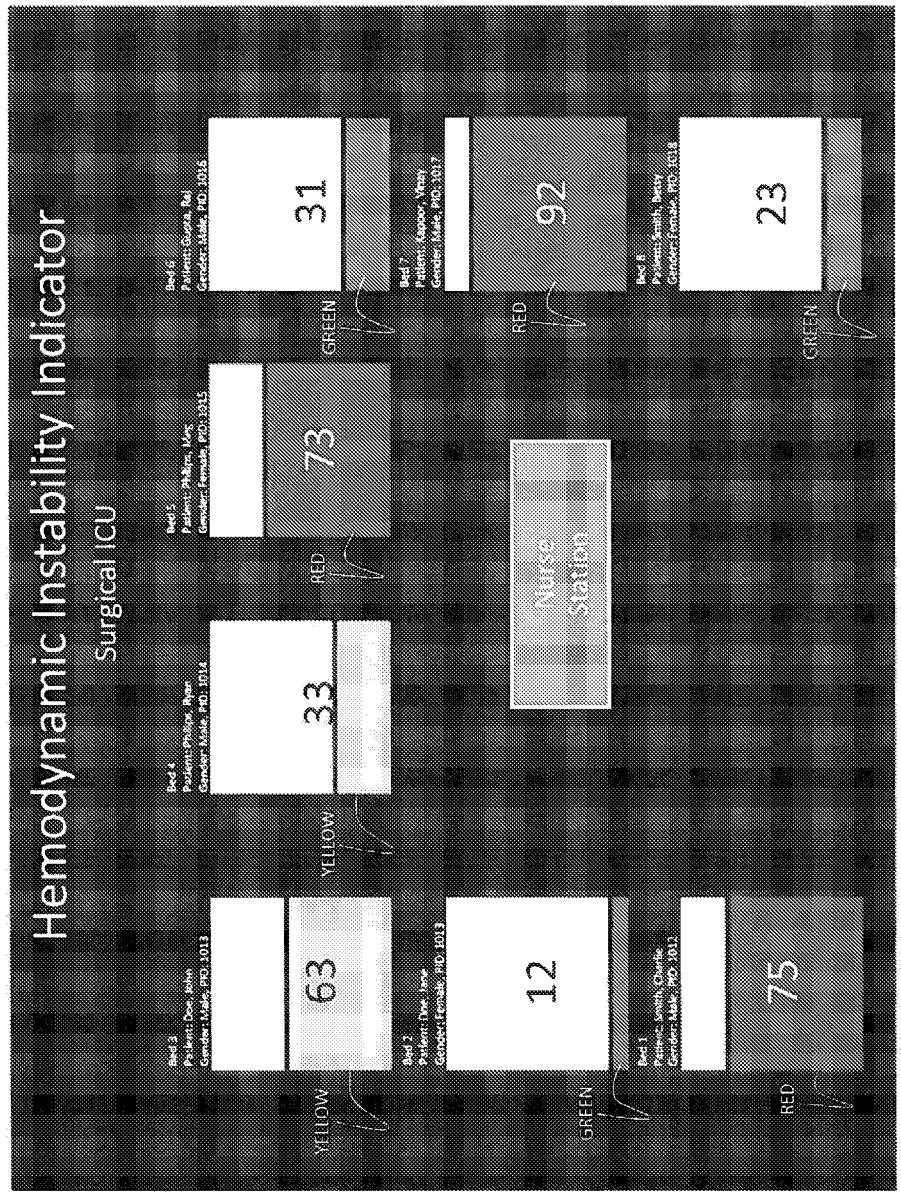
FIG. 8 is a graphical user interface (GUI) displaying deterioration indicator values for a plurality of beds.

With reference to FIG. 8, a graphical user interface (GUI) displays the deterioration indicator values for a plurality of beds to a clinician (e.g., at a nurse station). For example, the deterioration indicator can be displayed with one or more of a text value between 0 and 100 representing the value, a color to indicate low, medium, or high risk, and a bar chart volume representing the value. Values of 0 to 33.33 can be displayed with a green background (i.e., low risk), values between 33.33 and 66.66 can be displayed with a yellow background (i.e., medium risk), and all values greater than 66.66 can be displayed with a red background (i.e., high-risk). Labels proximate the deterioration indicators identify the corresponding patient by, for example, one or more of the patient's name and a patient identifier (PID). Other information, such as gender, can also be displayed. As illustrated, the deterioration indicators are displayed for hemodynamic instability, but the GUI is amenable to deterioration indicators for other physiological conditions.

Figure 9:
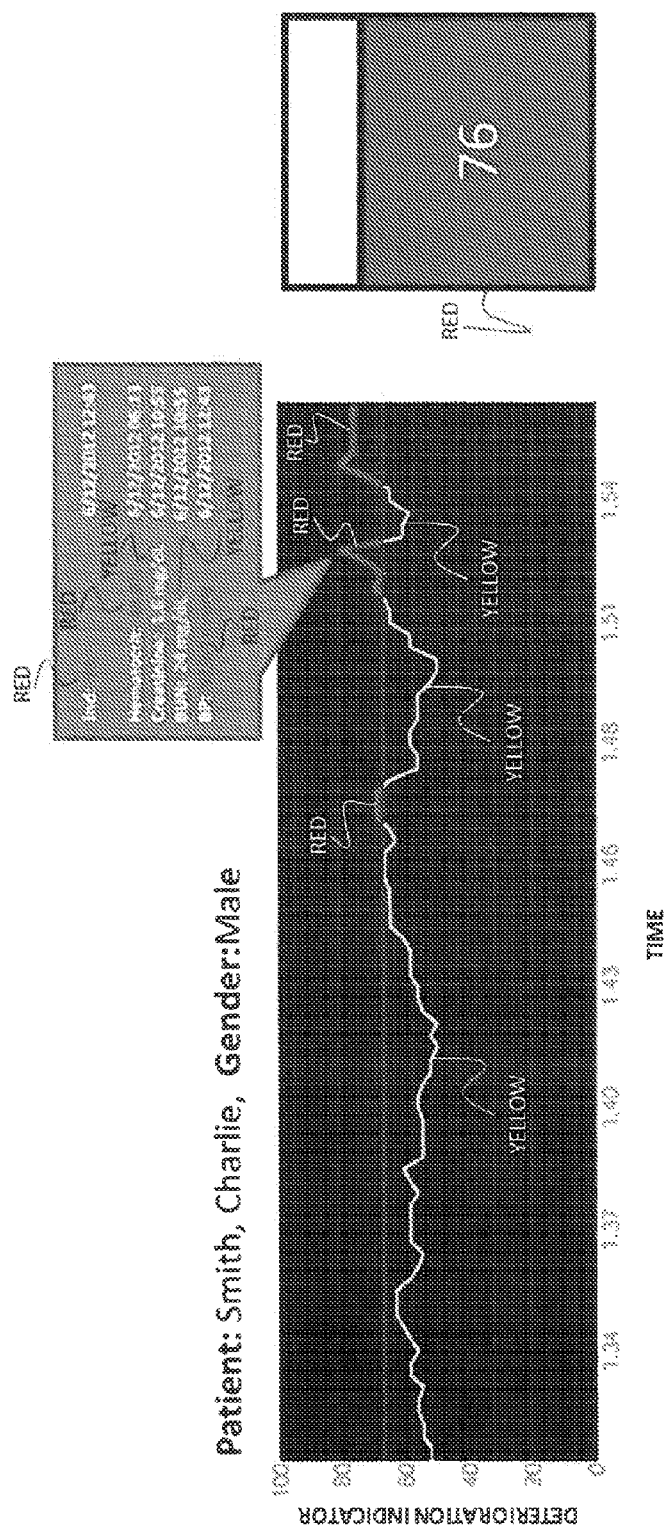
FIG. 9 is a GUI displaying detailed information regarding a deterioration indicator value.

With reference to FIG. 9, when a deterioration indicator is selected with, for example, a user input device, the GUI displays additional information regarding the selected deterioration indicator can be shown. This additional information can include a history of the patient's deterioration indicator over a predetermined period, such as three or six hours. The history can be displayed as a trend line of deterioration indicator values, as illustrated. The trend line can be color coded based on the risk region of the value at that point in time. As noted above, values of 0 to 33.33 can be displayed with a green background (i.e., low risk), values between 33.33 and 66.66 can be displayed with a yellow background (i.e., medium risk), and all values greater than 66.66 can be displayed with a red background (i.e., high-risk).

As a clinician selects a deterioration indicator value (e.g., by dragging a mouse cursor over the trend line), a tool-tip is shown for the selected deterioration indicator value, in this case 78. The tool-tip displays one or more of physiological parameters, lab parameters, and other relevant data for the deterioration indicator value. Such relevant data can include, for example, one or more of blood pressure, BUN, hematocrit, and other important laboratory and vital sign values. Further, such relevant data can include when displayed values were measured. Any values that are out of range can be highlighted in red or yellow to draw a clinician's attention to important pathophysiological issues that may be present.

The current deterioration indicator value can also be displayed next to the historical display, typically in the same manner shown in FIG. 8. For example, the current deterioration indicator value can be represented as a bar chart with the volume and color reflecting the degree of risk, and a number, in this case 76, positioned over the bar chart.

Figure 10:
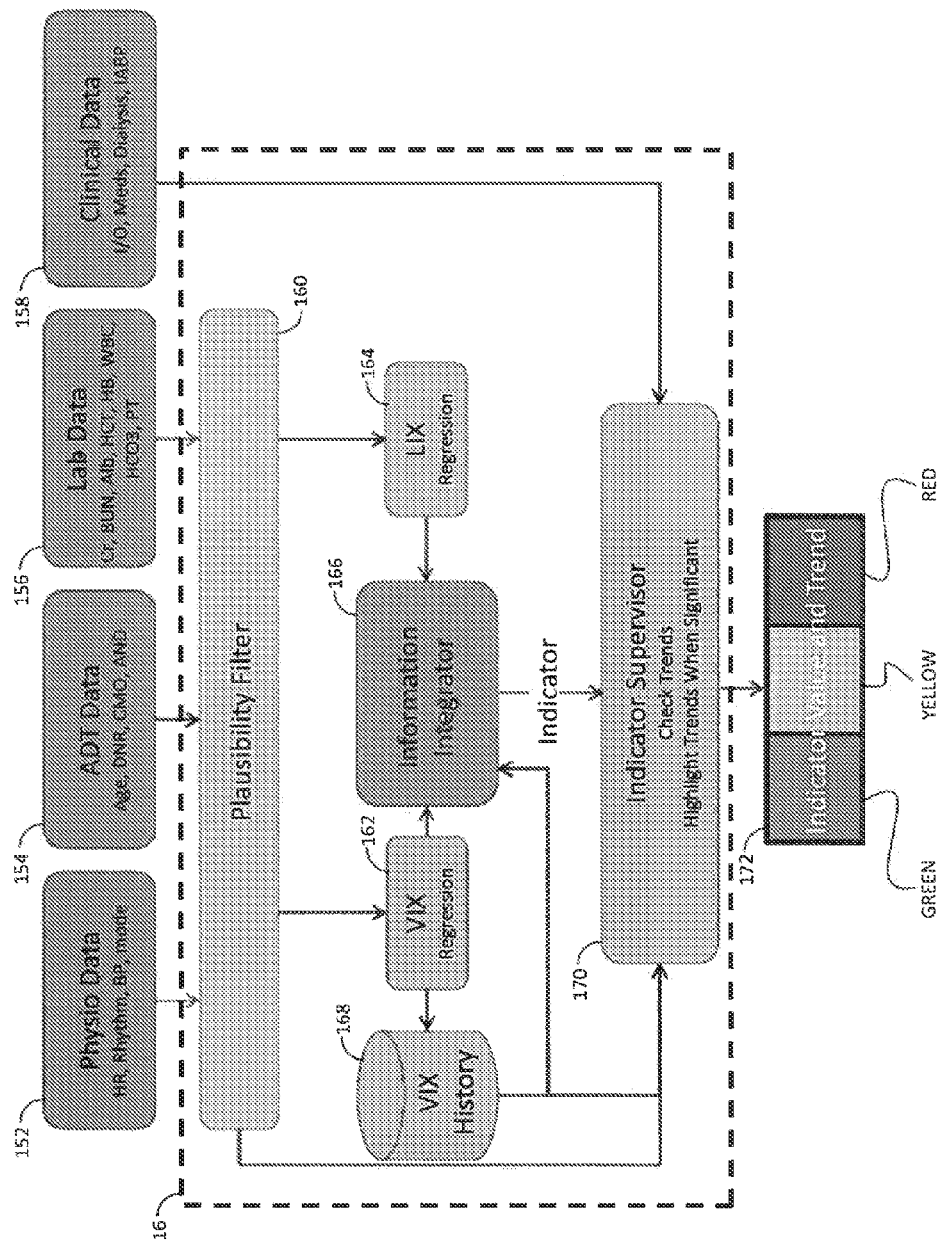
FIG. 10 is a flow chart illustrating operation of an alternative embodiment of the CDSS of FIG. 1.

The functionality regarding the deterioration indicator, described above, can be implemented within the components 12, 14, 16, 18, typically the CDSS 16, of the IT infrastructure 10 of FIG. 1. With reference to FIG. 10, a flow chart illustrating operation of an alternative embodiment of the CDSS 16 of FIG. 1 is illustrated. In contrast with the embodiment described in connection with FIG. 1, this embodiment pertains to the determination and use of the deterioration indicator described above. The components of the CDSS 16 of FIG. 1 are as described above, except that the processors 84 are reprogrammed.

According to the flowchart, the CDSS 16 receives patient data from a physiological data feed 152, an ADT data feed 154, a laboratory data feed 156, and a clinical data feed 158. As illustrated, the physiological feed 152 provides measurements for HR, heart rhythm status, BP (invasive and/or noninvasive), and mode (i.e., whether a noninvasive or invasive mode is being used); the ADT data feed 154 provides a patient's age, whether a patient does not want to be resuscitated, whether a patient wants comfort measures only, and whether a patient wants to allow a natural death; the laboratory data feed 156 provides lab results for blood tests, including tests for Cr, BUN, Alb, HCT, HB, WBC, HCO3, and PT; and the clinical data feed 158 describes medications (Meds) provided to a patient, whether the patient is administered dialysis, whether a patient has IABP, any other drugs and the like administered to a patient and any samples drawn from a patient. Typically, the data feeds 152, 154, 156, 158 are the patient data producers 12, shown in FIG. 1.

Typically, at least some of the patient data, including physiological data, ADT data and laboratory data, passes through a filter 160. The filter 160 standardizes the format of the data and/or ensures the parameters of the data being filtered are within plausible ranges. For example, the filter 160 ensures the patient age is reasonable and exceeds a predetermined age, such as the age of majority (e.g., generally 18 in the United States). Typically, the filter 160 is the same as, or otherwise includes, the filter 40 of FIG. 1.

A VIX module 162 and a LIX module 164 generate VIX (i.e., iVIX and/or nVIX) and LIX values (i.e., iLIX and/or nLIX), respectively, from the received patient data, optionally as filtered. The VIX and LIX values are determined as described above in connection with the generation of the deterioration indicator. Typically, the VIX module 162 is the same as, or otherwise includes, the VIX module 42 of FIGURE. Further, the LIX module 164 is typically a variant of the VIX module 162 augmented to generate an instability index of a physiological condition using only lab values. Typically, the VIX module 162 and/or the LIX module 164 use logistic regression models. However, other models can be employed.

Although not shown, it is contemplated that the models used by the VIX module 162 and/or the LIX module 164 can be selected by a rule supervisor and selector module. The rule supervisor and selector module uses the received patient data, optionally as filtered, to determine one or more VIX models and/or one or more LIX models to employ for the patient to be monitored. Typically, the available models include noninvasive and invasive variants for both LIX and VIX, since the models vary based on whether invasive or noninvasive. The rule supervisor and selector module uses the received patient data to provide a context for the patient and based on this context, the appropriate models are selected. The rule supervisor and selector module is typically a variant of the rule supervisor and selector module 56 of FIG. 1, the rule supervisor and selector module 56 of FIG. 1 extended for LIX model selection.

An information integrator module 166 receives LIX and VIX values from the LIX and VIX modules 162, 164 and generates deterioration indicator values, as described above. As to the latter, the LIX and VIX values are used to generate prevalence values using the VIX-to-prevalence table. Finally, the prevalence values are mapped to deterioration indicator values using Equation 3.

Typically, before generating deterioration indicator values, the information integrator module 166 filters the VIX values using VIX baseline values to remove outliers, as described above. The VIX baseline values are typically determined as described above using a VIX history database 168, which stores VIX values generated by the VIX module 162. The VIX baseline values typically include upper bVIX values and lower bVIX values. As described above, a upper bVIX value is the maximum VIX value, or a percentile, such as 90 percentile, over a previous period of time (e.g., the three preceding hours). Further, a lower bVIX value is the minimum VIX value, or a percentile, such as 10 percentile, over a previous period of time (e.g., the three preceding hours).

After determining a deterioration indictor value, the deterioration indicator value can be displayed, as described above. For example, a deterioration indicator value can be directly or indirectly displayed to a clinician, for example, using the patient data consumers 18 of FIG. 1. As to the former, for example, the final value can be displayed to a clinician using text, a bar chart, or the like. As to the latter, for example, the range of indicator values can be divided into bands corresponding to the risk of patient deterioration. The final indicator can then be mapped to one of these bands and the band can be identified to a clinician. The band is typically identified to a clinician using colors. The GUI of FIGS. 8 and 9 can, for example, be used to display deterioration indicator values.

An optional indicator supervisor 170 receives the deterioration indicator values and corresponding VIX data from the information integrator 166 and the VIX history database 168, respectively. Using the received VIX data, the indicator supervisor 170 can monitor VIX trends and mark VIX values for possible alerting using the re-arming method, described above. As noted above, the re-arming method is controlled by max_vix, marking VIX values that are higher than max_vix (by some threshold) and re-setting max_vix to the current value of VIX. Further, max_vix can be re-set to the current VIX if the current VIX drops to a specified fraction of max_vix.

When marked VIX values exceed an alert threshold, the corresponding deterioration indicator, when displayed, can be highlighted. The deterioration indicator can be displayed as described above, for example, using the GUI of FIGS. 8 and 9. As illustrated, a display 172 of deterioration indicator values and corresponding trends is used with color coding. Additionally, or alternatively, when marked VIX values exceed an alert threshold, alerts can be generated to, for example, notify clinicians.

At least one of the processors 28, 80, 82, 84 of FIG. 1, typically the processors 84 of the CDSS 16, execute processor executable instructions embodying the foregoing functionality, including the functionality of the filter 160, the VIX module 162, the LIX module 164, the information aggregator 166, and the indicator supervisor 170. The processor executable instructions are suitably embodied by corresponding memories 86, 88, 90, 92 of the processors 28, 80, 82, 84. At least one of the memories 86, 88, 90, 92, typically the memories 92 of the CDSS 16, include the VIX history database 168.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field-programmable gate array (FPGA), and the like; a user input device includes one or more of a mouse, a keyboard, a touch screen display, one or more buttons, one or more switches, one or more toggles, and the like; a display device includes one or more of a liquid crystal display (LCD), an light emitting diode (LED) display, a plasma display, a projection display, a touch screen display, and the like; and databases include one or more memories.

The invention has been described with reference to the preferred embodiments. Modifications and alterations may occur to others upon reading and understanding the preceding detailed description. For example, while VIX was discussed as a means of detecting unstable patients, VIX could also be used to determine which patients are in a safely stable state in order to prioritize his/her time or to decide who can be moved from, for example, the ICU to the general ward, since a prolonged, very low VIX value is indicative of a very stable patient. It is intended that the invention be construed as including all such modifications and alterations insofar as they come within the scope of the appended claims or the equivalents thereof.

The invention claimed is:

1. A medical system for monitoring a patient, said system comprising:
   one or more processors programmed to:
      receive patient data for the patient, the patient data including vital sign measurements and laboratory results;
      calculate a vital signs instability index (VIX) regarding a physiological condition of the patient from the received vital sign measurements;

calculate a laboratory instability index (LIX) regarding the physiological condition from the received laboratory results; and integrate the VIX and the LIX into an indicator of patient deterioration, wherein the integration includes:

looking up a prevalence value in a VIX-to-prevalence table using the VIX and the LIX, the prevalence value indicating a prevalence of unstable VIX segments in a training population for differing VIX ranges and LIX bands, the VIX ranges spanning the range of possible values for the VIX in predetermined increments, the LIX bands representing differing degrees of risk with the physiological condition and including the range of possible values for the LIX, wherein the VIX segments of the training population correspond to VIX trends over a predetermined period of time; and mapping the prevalence value to a value of the indicator by linearly adjusting the prevalence value so it scales over the range of prevalence values in the VIX-to-prevalence table.

2. The medical system according to claim 1, wherein the LIX is calculated using a model modeling the relationship between instability of the physiological condition and the laboratory tests corresponding to the received laboratory results.

3. The medical system according to claim 1, wherein the at least one processor is further programmed to:

filter VIX to remove outlying values using an upper baseline and a lower baseline, an upper baseline value being a maximum VIX value over a previous period of time, and a lower baseline value being a the minimum VIX value over a previous period of time.

4. The medical system according to claim 3, wherein a VIX value is suppressed if it exceeds a predetermined fraction of corresponding upper baseline value or is less than a predetermined fraction of a corresponding lower baseline value.

5. The medical system according to claim 1, wherein that at least one processor is further programmed to:

display the indicator using one or more of text, color coding, and a bar chart, the color codes identifying different degrees of risk of patient deterioration.

6. The medical system according to claim 5, wherein that at least one processor is further configured to:

in response to detecting significant patient deterioration using the VIX, independent of the indicator, highlight the display of the indicator.

7. The medical system according to claim 1, wherein that at least one processor is further programmed to:

display a trend line of selectable values of the indicator; and upon selection of one of the selectable values, display a tool-tip including one or more of vital sign measurements, lab results, and other relevant data for the selected value.

8. A medical method for monitoring a patient, said method being performed by at least one processor and comprising:

receiving patient data for the patient, the patient data including vital sign measurements and laboratory results;

calculating a vital signs instability index (VIX) regarding a physiological condition of the patient from the received vital sign measurements;

calculating a laboratory instability index (LIX) regarding the physiological condition from the received laboratory results; and integrating the VIX and the LIX into an indicator of patient deterioration, wherein the integrating includes:

looking up a prevalence value in a VIX-to-prevalence table using the VIX and the LIX, the prevalence value indicating a prevalence of unstable VIX segments in a training population for differing VIX ranges and LIX bands, the VIX ranges spanning the range of possible values for the VIX in predetermined increments, the LIX bands representing differing degrees of risk with the physiological condition and including the range of possible values for the LIX, wherein the VIX segments of the training population correspond to VIX trends over a predetermined period of time; and mapping the prevalence value to a value of the indicator by linearly adjusting the prevalence value so it scales over the range of prevalence values in the VIX-to-prevalence table.

9. The medical method according to claim 8, wherein the LIX is calculated using a model modeling the relationship between instability of the physiological condition and the laboratory tests corresponding to the received laboratory results.

10. The medical method according to claim 8, further including:

filtering VIX to remove outlying values using an upper baseline and a lower baseline, an upper baseline value being a maximum VIX value over a previous period of time, and a lower baseline value being a the minimum VIX value over a previous period of time.

11. The medical method according to claim 8, wherein that at least one processor is further programmed to:

display the indicator using one or more of text, color coding, and a bar chart, the color codes identifying different degrees of risk of patient deterioration.

12. The medical method according to claim 8, further including:

displaying a trend line of selectable values of the indicator; and upon selection of one of the selectable values, displaying a tool-tip including one or more of vital sign measurements, lab results, and other relevant data for the selected value.

13. At least one processors programmed to perform the method according to claim 8.

14. A non-transitory computer readable medium carrying software which controls one or more processors to perform the method according to claim 8.

* * * * *